United States Patent
Noo et al.

(10) Patent No.: US 9,600,924 B2
(45) Date of Patent: Mar. 21, 2017

(54) ITERATIVE RECONSTRUCTION OF IMAGE DATA IN CT

(71) Applicants: SIEMENS AKTIENGESELLSCHAFT, Munich (DE); UNIVERSITY OF UTAH, Salt Lake City, UT (US)

(72) Inventors: Frédéric Noo, Midvale, UT (US); Katharina Schmitt, Fuerth (DE); Harald Schöndube, Erlangen (DE)

(73) Assignees: SIEMENS AKTIENGESELLSCHAFT, Munich (DE); UNIVERSITY OF UTAH, Salt Lake City, UT (US)

( * ) Notice: Subject to any disclaimer, the term of this patent is extended or adjusted under 35 U.S.C. 154(b) by 510 days.

(21) Appl. No.: 14/172,957

(22) Filed: Feb. 5, 2014

(65) Prior Publication Data

US 2015/0221124 A1    Aug. 6, 2015

(51) Int. Cl.
    *G06K 9/00*    (2006.01)
    *G06T 15/08*   (2011.01)
    *G01N 23/04*   (2006.01)
    *G06T 7/00*    (2006.01)
    (Continued)

(52) U.S. Cl.
    CPC .......... *G06T 15/08* (2013.01); *G01N 23/046* (2013.01); *G06T 7/0012* (2013.01); *G06T 11/003* (2013.01); *G06T 11/006* (2013.01); *G06T 17/00* (2013.01); *G06T 2207/10081* (2013.01); *G06T 2211/424* (2013.01)

(58) Field of Classification Search
    None
    See application file for complete search history.

(56) References Cited

U.S. PATENT DOCUMENTS 8,571,287 B2 * 10/2013 DeMan ............... G01N 23/046
                                                    382/131
2007/0297656 A1 * 12/2007 DeMan ............... G01N 23/046
                                                    382/128
(Continued)

OTHER PUBLICATIONS

De Man et al.: Distance-driven projection and backprojection in three dimensions; Phys. Med. Biol., vol. 49, No. 11, pp. 2463-2475; 2004; Jun. 7, 2004.
(Continued)

*Primary Examiner* — Jason Heidemann
(74) *Attorney, Agent, or Firm* — Harness, Dickey & Pierce, P.L.C.

(57) ABSTRACT

A method and calculation unit are disclosed for reconstructing an image from measured projection data. In an embodiment, the method includes reconstructing an initial image from the projection data via back-projection; dividing the initial image into contiguous blocks of voxels; defining groups of voxels, wherein each group is defined by selecting one voxel from each block, each voxel having the same position relative to the other voxels within its block; updating the voxel values for all voxels within one group by minimizing a function consisting of a weighted sum of a first term representing the geometry of the data acquisition process, and a second regularization term; and repeating the updating of the voxel values for all voxels within one group until all groups have been updated at least once.

25 Claims, 6 Drawing Sheets

(51) Int. Cl.
*G06T 11/00* (2006.01)
*G06T 17/00* (2006.01)

(56) References Cited

U.S. PATENT DOCUMENTS

| | | | | |
|---|---|---|---|---|
| 2009/0123048 A1* | 5/2009 | Leroux | G06T 11/006 | 382/131 |
| 2011/0188724 A1* | 8/2011 | Bruder | A61B 6/032 | 382/131 |
| 2011/0262054 A1* | 10/2011 | Benson | G01N 23/046 | 382/275 |
| 2011/0268335 A1* | 11/2011 | Kunze | A61B 6/032 | 382/131 |
| 2012/0155728 A1* | 6/2012 | DeMan | G06T 11/006 | 382/131 |
| 2014/0198892 A1* | 7/2014 | Yamakawa | A61B 6/032 | 378/4 |
| 2014/0294147 A1* | 10/2014 | Chen | G01V 5/0016 | 378/57 |
| 2015/0078506 A1* | 3/2015 | Noo | G06T 11/003 | 378/4 |

OTHER PUBLICATIONS

Thibault Jean-Baptiste et al., "A three-dimensional statistical approach to improved image quality for multislice helical CT"; in: Medical Physics, vol. 34, No. 11, Nov. 2007; pp. 4526-4544; DOI: 10.1118/1.2789499.

Grouped-Coordinate Ascent Algorithms for Penalized-Likelihood Transmission Image Reconstruction Jeffrey A. Fessler, Edward P. Ficaro, Neal H. Clinthorne and Kenneth Lange IEEE Transactions on Medical Imaging, vol. 16,No. 2, Apr. 1997 p. 166-175; 1997.

Axial block coordinate descent (ABCD) algorithm for X-ray CT image reconstruction Jeffrey A. Fessler and Donghwan Kim 11th International Meeting on Fully Three-Dimensional Image Reconstruction in Radiology and Nuclear Medicine p. 262-265.

Beck et al., "A fast iterative shrinkage-thresholding algorithm for linear inverse problems", 2009, SIAM J. Imaging Sci. 2, pp. 183-202; 2009.

Kamphuis et al.: "Accelerated iterative transmission CT reconstruction using an ordered subsets convex algorithm"; IEEE Transactions on Medical Imaging; vol. 17; No. 6; pp. 1001-1105; 1998.

Fessler et al.: "Conjugate-gradient preconditioning methods for shift-variant PET image reconstruction"; in: IEEE Transactions on Image Processing; vol. 8; No. 5; pp. 688-699; 1999.

Daubechies et al.: "An iterative thresholding algorithm for linear inverse problems with a sparsity constraint"; Communications on Pure and Applied Mathematics, vol. LVII 57; pp. 1413-1457; 2004.

Benson et al.: "Block-based iterative coordinate descent"; Proc. IEEE Nuc. Sci. Symp. Med. Im. Conf. 2010; pp. 2856-2859; 2010.

Erdogan et al.: "Ordered subsets algorithm for transmission tomography"; Phys. Med. Biol. 44 (11), pp. 2835-2851 (1999).

\* cited by examiner

ITERATIVE RECONSTRUCTION OF IMAGE DATA IN CT

FIELD

At least one embodiment of the present invention generally relates to a method for reconstructing an image dataset of an object from projection data, wherein the projection data was acquired from the object via an x-ray computed tomography (CT) system. Further embodiments of the invention also generally relate to a calculation unit for the reconstruction of an image dataset of an object from projection data, a computed tomography system comprising such a calculation unit, and/or a data carrier comprising program code for performing at least one embodiment of the inventive method.

BACKGROUND

In x-ray computed tomography, the object from which projection data is to be acquired is generally exposed to x-ray radiation from a number of projection directions. An image dataset is then reconstructed from the projection data. This is generally done using a back-projection method, wherein the projection data is often pre-processed. For example, a so-called rebinning step is often performed, in which the projection data generated from a fan-shaped beam of x-rays is rearranged, so that it is in such a form as if the x-ray beams had been parallel. The data that has been thus rearranged and filtered is then used for a back-projection onto individual image points or voxels within the volume of interest.

One standard method generally used for the reconstruction is a so-called filtered back-projection method (FBP). With this method, the rebinned data is generally first transformed into the frequency range, where filtering takes place by multiplication using a convolution kernel. The filtered data is then back-transformed and the back-projection is done on the filtered data. The selection of the convolution kernel allows the desired image characteristics, in particular image sharpeners and noise, to be influenced. One algorithm often used is the so-called Feldkamp algorithm.

However, simple back-projection methods have the disadvantage that they do not produce satisfactory results when the projection data is incomplete, for example when the projection directions do not cover an angle of 180° plus the fan beam angle around the object, or the object is not fully within the field-of-view of all projections. They also are not able to fully account for statistical properties of the data.

Other reconstructions methods which have more recently been developed are iterative image reconstruction methods. In such an iterative reconstruction method, a reconstruction of initial image data from the measured projection data takes place first. From this initial image data, a "projector" (projection operator), which should map the projection geometry of the CT-system and the data acquisition process mathematically as closely as possible, is then used to generate synthetic projection data. The difference in respect of the measured projection data is then back-projected, thereby reconstructing a residue image, which can be used to update the initial image. The updated image data can in turn be used to generate new synthetic projection data in a next iteration step with the aid of a projection operator, to form the difference to the measurement signals again and to calculate a new residue image, which can in turn be used to improve the image data of the current iteration stage.

However, these iterative image reconstruction algorithms often do not converge fast, and are therefore very computation-intensive. Several reconstruction algorithms based on the penalized weighted least-square model have been suggested. However, no iterative reconstruction method is currently considered as satisfactory for routine clinical usage.

The so-called FISTA (fast iterative shrinkage-thresholding algorithm) is one algorithm for statistical iterative reconstruction methods for x-ray CT. It updates all voxels simultaneously with a fast outer converging loop. However, the method is hampered by the need to solve a non-linear image denoising problem with correlated voxels at each iteration. FISTA is described in the paper by Amir Beck and Marc Teboulle "A Fast Iterative Shrinkage-Thresholding Algorithm for Linear Inverse Problems" SIAM, J. Imaging Sciences, Vol. 2, No. 1, pp. 183-202. The content of this paper is hereby incorporated herein by reference in its entirety.

SUMMARY

Embodiments of the present invention provide an iterative reconstruction method for CT data, a corresponding calculation unit and data carrier including suitable program code to execute at least one embodiment of the method, which improve upon or even overcomes the at least one of above disadvantages of the prior art methods. In particular, at least one embodiment of the present invention provides a reconstruction method which converges fast, is generally fast and stable, can cope with incomplete or sparse data in order to allow a reduction in dose imparted to the patient, and can fully account for statistical properties of the data.

At least one embodiment of the present invention is directed to a method for the reconstruction of an image dataset of an object from projection data, wherein the projection data was acquired from the object by means of an x-ray computed tomography system, the method comprising reconstructing an initial image dataset from the projection data via a back-projection algorithm;

dividing the initial image dataset into blocks of voxels, each block having at least approximately the same dimensions, defining groups of voxels within the first image dataset, wherein each group is defined by selecting one voxel from each block, each voxel within one group having the same position relative to the other voxels within its block, wherein the voxels within one group define a subspace;

updating the voxel values for all voxels within one group by minimizing a function consisting of a weighted sum of a first term representing at least the geometry of the data acquisition process, and a second term, which is preferably a regularization term, to thereby generate an intermediate image dataset; and repeating the updating of the voxel values for all voxels within one group, using the intermediate image dataset as input, until all groups of voxels have been updated at least once, whereby a final image dataset is obtained.

At least one embodiment of the invention is also directed to a corresponding calculation unit for the reconstruction of an image dataset of an object from projection data which is suitable to carry out at least one embodiment of the inventive method. According to at least one embodiment, it will comprise at least a first data storage unit for storing the projection data and the final image dataset, and which may be a hard disc, server, USB-stick optical or other long-term storage. It may further comprise a second data storage unit for storing the intermediate image datasets, wherein this data storage component may be a faster and more temporary component, such as the working memory of a computer.

The calculation unit also requires a data processing unit for reconstructing the first image dataset, and for performing the updating steps. Such data processing unit may be any computer-type computation component, for example the CPU of a PC or other workstation or computer. Generally, the calculation unit may be part of any type of computer, laptop, portable device, and of course any acquisition system for medical images. In at least on embodiment, the calculation unit will also include an image dataset interface for outputting the final image dataset, for example a screen, display or printer. According to at least one embodiment, the calculation unit will also include a data interface for transferring projection data acquired using an x-ray computed tomography apparatus.

Such a calculation unit can be part of a computed tomography system including a rotatable projection data acquisition unit including an x-ray source and a detector for acquiring projection data of an object.

Embodiments of the method can be implemented in the form of software, for example on the calculation unit or the computed tomography system. At least one embodiment of the invention is also directed to a digital data carrier comprising program code of a computer program which is capable of implementing a method according to any embodiment of the inventive method, when the computer program is executed on a computer. At least one embodiment of the invention is also directed to a computer program product, which can be loaded into a data storage unit of a programmable calculation unit, which may be part of a computed tomography system.

Further advantageous embodiments and developments of the invention will emerge from the dependent claims and the description which follows. A method or subject matter of one claim category can also be developed in the same way as the dependent claims of a different claim category. Further, the subject-matter of all dependent claims may be combined with each other.

BRIEF DESCRIPTION OF THE DRAWINGS

The invention is described in more detail below with reference to the accompanying drawings based on example embodiments. Like components are assigned the same reference signs in the figures.

DETAILED DESCRIPTION OF THE EXAMPLE EMBODIMENTS

Figure 1:
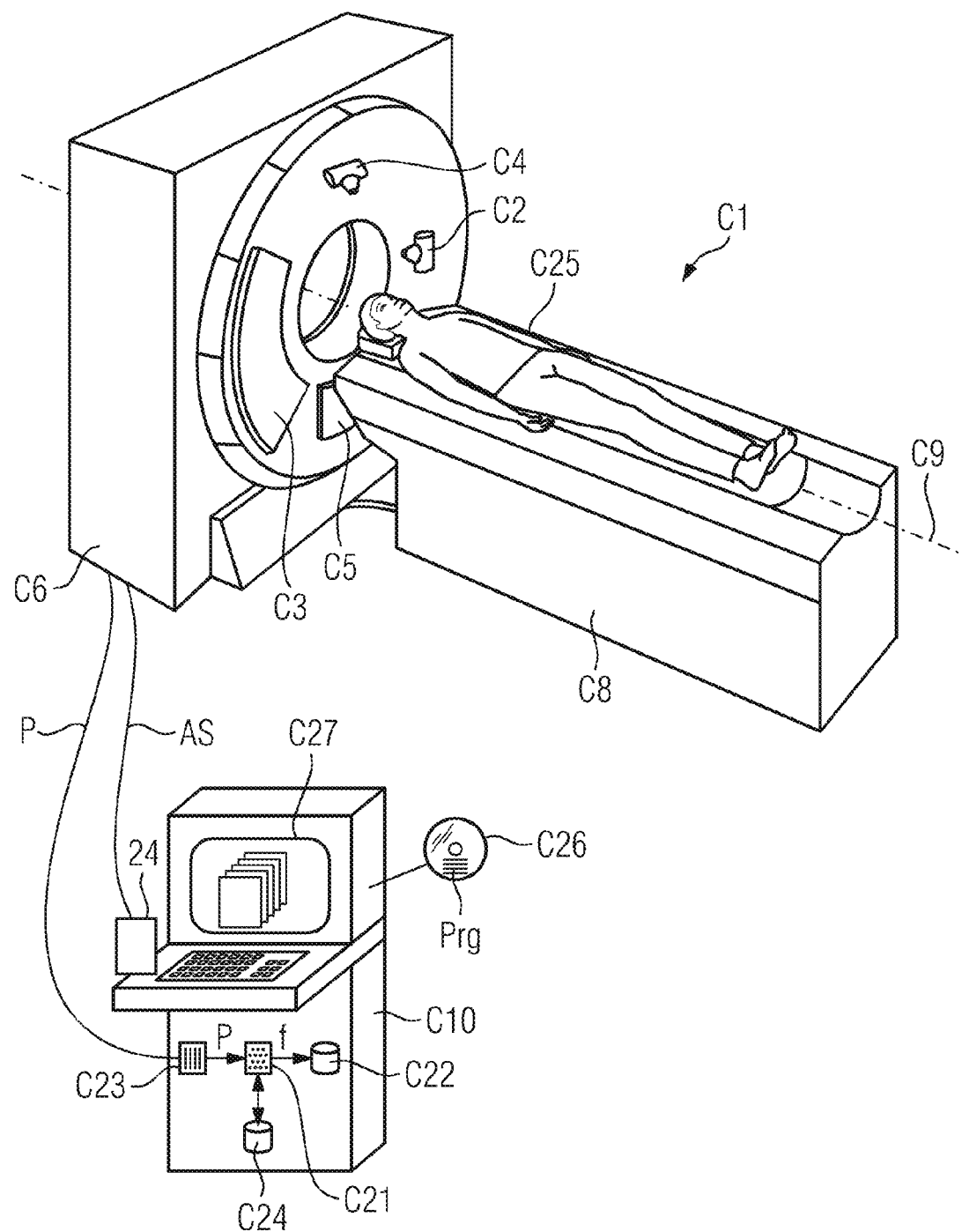
FIG. 1 shows a schematic representation of a first example embodiment of a computed tomography system having an image reconstruction facility.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the present invention is directed to a method for the reconstruction of an image dataset of an object from projection data, wherein the projection data was acquired from the object by means of an x-ray computed tomography system, the method comprising reconstructing an initial image dataset from the projection data via a back-projection algorithm;

dividing the initial image dataset into blocks of voxels, each block having at least approximately the same dimensions, defining groups of voxels within the first image dataset, wherein each group is defined by selecting one voxel from each block, each voxel within one group having the same position relative to the other voxels within its block, wherein the voxels within one group define a subspace;

updating the voxel values for all voxels within one group by minimizing a function consisting of a weighted sum of a first term representing at least the geometry of the data acquisition process, and a second term, which is preferably a regularization term, to thereby generate an intermediate image dataset; and repeating the updating of the voxel values for all voxels within one group, using the intermediate image dataset as input, until all groups of voxels have been updated at least once, whereby a final image dataset is obtained.

In at least one embodiment of the present invention, the final image dataset has good quality, even when the inputted measured projection data was incomplete or sparse. In at least one embodiment of the invention, the iterative reconstruction method can be conducted at least in part by parallel processing, wherein several calculation steps may be performed in parallel.

At least one embodiment of the invention is also directed to a corresponding calculation unit for the reconstruction of an image dataset of an object from projection data which is suitable to carry out at least one embodiment of the inventive method. According to at least one embodiment, it will comprise at least a first data storage unit for storing the projection data and the final image dataset, and which may be a hard disc, server, USB-stick optical or other long-term storage. It may further comprise a second data storage unit for storing the intermediate image datasets, wherein this data storage component may be a faster and more temporary component, such as the working memory of a computer.

The calculation unit also requires a data processing unit for reconstructing the first image dataset, and for performing the updating steps. Such data processing unit may be any computer-type computation component, for example the CPU of a PC or other workstation or computer. Generally, the calculation unit may be part of any type of computer, laptop, portable device, and of course any acquisition system for medical images. In at least on embodiment, the calculation unit will also include an image dataset interface for outputting the final image dataset, for example a screen, display or printer. According to at least one embodiment, the calculation unit will also include a data interface for transferring projection data acquired using an x-ray computed tomography apparatus.

Such a calculation unit can be part of a computed tomography system including a rotatable projection data acquisition unit including an x-ray source and a detector for acquiring projection data of an object.

Embodiments of the method can be implemented in the form of software, for example on the calculation unit or the computed tomography system. At least one embodiment of the invention is also directed to a digital data carrier comprising program code of a computer program which is capable of implementing a method according to any embodiment of the inventive method, when the computer program is executed on a computer. At least one embodiment of the invention is also directed to a computer program product, which can be loaded into a data storage unit of a programmable calculation unit, which may be part of a computed tomography system.

Further advantageous embodiments and developments of the invention will emerge from the dependent claims and the description which follows. A method or subject matter of one claim category can also be developed in the same way as the dependent claims of a different claim category. Further, the subject-matter of all dependent claims may be combined with each other.

At least one embodiment of the inventive method uses an image dataset from projection data acquired from an object using an x-ray computed tomography system as input. In some embodiments of the invention, the method may include a step of acquiring the projection data from the object by means of an x-ray computed tomography system. The object may be part of the human or animal body, in particular a patient. The x-ray computed tomography system may be a CT-scanner using fan beams or cone beams to generate one- or two-dimensional projection data. The projection data may be acquired in different manners, e.g. using a sequential method and also using a helical method.

The x-ray computed tomography system may use cone beams to acquire projection data from the object, wherein the x-ray source and the detector are often arranged on opposite ends of a C-arm, which can be rotated around the patient table in order to acquire projection data from a number of projection directions.

First, an initial image dataset is reconstructed from the projection data by means of a back-projection, which can be a standard back projection method, such as the filtered back projection described above, in particular using the Feldkamp algorithm. In at least one embodiment of the inventive method, the initial image dataset is then smoothed, for example by using a low-pass filter, and wherein edge-preserving methods can optionally be used. In some embodiments of the invention, the initial image dataset is a two-dimensional image dataset, in other embodiments, it is a three-dimensional (3D) image dataset. For simplicity, the image data points shall be referred to herein as voxels, rather than pixels, even if the image dataset is two-dimensional.

In reconstructing the initial image dataset, the projection data can be pre-processed first, as described above. For example, the measured projection data can first be filtered and stripped of noise as far as possible, after which a rebinning step can also be performed if required. The projection data can also be subjected beforehand to other correction methods, e.g. beam hardening correction.

In at least one embodiment of the invention, the projection data is incomplete, therefore cannot be reconstructed with good quality by back projection methods. "Complete" in this context means for example that each volume element of the object to be examined must be irradiated over a projection angle range of 180° plus the fan angle if the measurement is carried out in fan-beam geometry, or plus the cone angle if the measurement is being carried out in cone-beam geometry. An incomplete dataset is for example present if this condition is not fulfilled.

According to embodiments of the invention, the initial image dataset is divided into blocks of voxels, each block having at least approximately the same size, e.g. number of voxels and dimensions. In most embodiments, the blocks will have exactly the same dimension or size, for example m×n in case of 2D images, or m×n×o in case of 3D images. In many embodiments of the invention, the blocks of voxels will be square or quadratic or cubic, i.e. incorporating m×m or m×m×m voxels. m, n and o may be integral numbers between 2 and 32, for example between 2 and 16 or 2 and 8, for example the blocks may have size 2×2, 3×3, 4×4 or 5×5. In most embodiments, each voxel in the initial image dataset will be part of one block. The blocks may be contiguous or not contiguous, in order to account for the desire to improve specific regions within the patient, or to perform the method of the invention only on specific regions of the initial dataset.

In the next steps, groups of voxels are defined, wherein each group of voxels is defined by selecting one voxel or element out of each block, using the same element position from one block to the next. The voxels within one group define a subspace. For example, all voxels at the upper left corner of each block belong to the same group and define a subspace.

In several embodiments of the invention, the voxel values, e.g. the grey scale value belonging to each voxel within one group in the initial image dataset, is then updated. Updating means that the voxel value is replaced by another voxel value which should in most instances be closer to the true image than the initial voxel value. This is done by minimizing a function consisting of a weighted sum of a first term, which is preferably a least squares expression representing at least the geometry of the data acquisition process, and a second term, which is a regularization term, preferably a non-linear regularization term. The regularization term is used to mitigate noise and artifacts. Example embodiments for this step will be given below. The updated voxel values are written into an intermediate image dataset. This intermediate image dataset is then used as input image dataset (instead of the initial image dataset) for another step of updating the voxel values for all voxels within another group. The updated voxel values are stored in another intermediate image dataset, which is used as input for another updating step of the third group of voxels. This process is repeated until all groups of voxels have been updated at least once. The update of all voxels within one group or subspace shall be called a sub-iteration in the following. The update of all subspaces at least once shall be called a full iteration.

According to advantageous embodiments of the present invention, all voxels within one subspace are updated simultaneously or in parallel, while the other voxel values remain unchanged. This considerably reduces computation time. It further makes the minimization problem more manageable, since the size of the forward projection matrix representing the geometry of the data acquisition unit is decreased by a factor of $m^2$ in two dimensions and $m^3$ in three dimensions. Further, the voxels within the subspace are not linked to each other by the non-linear regularization term, if this imposes constraints on voxels that are a distance less than m from each other, which will be the case in many embodiments. Therefore, in some embodiments the update is obtained using two nested loops: One outer Landweber-type loop, and one inner loop that corresponds to solving independent one-dimensional problems. This structure of the inner loop allows the most complicated, non-linear aspect of the iterative reconstruction problem to be handled using parallel processors. Moreover, in several embodiments each independent one-dimensional problem can be solved efficiently using the Newton-Raphson method. Additionally, the outer loop can be made more efficient using any technique that is known to accelerate Landweber iterations. In some embodiments, the Fast Iterative Shrinkage-Thresholding Algorithm (FISTA) method is used to accelerate the Landweber iterations.

One sub-iteration corresponds to updating the voxels within one subspace. In embodiments of the invention, this update is obtained as the solution of a sub-optimization problem, namely the minimization of the objective function $\Phi(x, g)$ with all voxel values being fixed except for those that are in the subspace. According to several embodiments of the invention, the exact solution is sought, not an approximate solution. For example, the minimization problem of updating the second term is calculated exactly, and/or the step of updating is performed by exactly solving the optimization problem corresponding to minimizing the function.

In most embodiments, the steps set out in claim 1 are performed in consecutive order, wherein additional steps may or may not be performed in between the cited steps.

The update of all voxels within one subspace is called a sub-iteration. In many embodiments of the present invention, the sub-iterations are carried out in a pre-determined order, to thereby promote convergence. According to one embodiment, the sub-iterations are performed in a "back-and-forth" scheme. Specifically, one starts with the first voxels in one corner of each block, for example the upper left corner and continuous by updating one voxel after another until the voxel in the opposite corner is reached, for example the lower right corner. In most embodiments, the voxels which are updated one after the other are adjoining. Once the last voxel in the opposite corner has been reached, in most embodiments one then goes back towards the first voxel in the block, in reverse order. Thereby, all voxels as updated twice, except the voxels in the opposite corner. A completed "back-and-forth" run is called a full iteration in this embodiment. In other words, one full iteration is performed by repeating the step of updating the voxel values for all voxels within one group until all groups of voxels have been updated once or twice in a predetermined order. In other embodiments, the full iteration may involve only one single or several independent updates of each voxel.

Different numbers of full iterations are performed in different embodiments, for example 1, 2, 3 or 4.

In several embodiments, the step of updating the voxel values for all voxels within a sub-space includes minimizing the function until a certain threshold is reached, wherein the threshold may be constant or may vary from one full iteration to the next. The threshold may be defined absolutely or as a relative term. Further, the decision whether another full iteration is performed may be made dependent on whether a certain threshold is reached.

Example embodiments of the minimization step are now described.

As mentioned above, the voxel values may be updated using a FISTA-type method, as described in the above-mentioned paper by Amir Beck and Marc Teboulle. In some embodiments of the invention, the first term is minimized using an iterative method, wherein in each iteration the voxels to be updated are forward projected to obtain a calculated projection dataset, the difference between the calculated projection dataset and the projection data is computed, the difference is backward projected into the image space, and the backward projection is weighted and subtracted from or added to the image dataset or in particular the voxels to be updated. In some embodiments, this minimization is performed using a Landweber algorithm. This is an algorithm to solve ill-posed linear inverse problems, which is known in the art.

In addition to the geometry of the data acquisition process, the first term may in some embodiments include a statistical component taking account of the measurement statistics, for example data redundancies and data variance.

The second term to be minimized is in some embodiments a non-linear regularization term to mitigate noise and artifacts. In some embodiments, it relates each voxel to be updated to its neighboring voxels, for example only the nearest neighbors. Thereby, the voxels within one group can be updated simultaneously, since these voxels are not nearest neighbors. In embodiments of the invention, the second term is selected so that the function is convex. Further, the second term may be minimized using a Newton-Raphson method. This is a method for numerical solution of non-linear equations. It is an iterative method, which however leads to an exact result, if sufficient iterations are performed. In the Newton-Raphson algorithm to solve the equation f(x)=0, the following calculation is repeated until the result is known with sufficient precision:

$$X_{n+1} = X_n - \frac{f(x_n)}{f'(x_n)}$$

Thus, only the first derivative f' of the function is used.

FIG. 1 shows a schematic representation of a computed tomography system C1 including a calculation unit C10 according to an embodiment of the invention. It is a CT device of the third generation, but the invention is not restricted to this, or to any particular CT device. In this embodiment, located in the gantry housing C6 is a closed gantry, not visible here, arranged on which are a first x-ray tube C2 with a detector C3 opposite, and optionally a second x-ray tube C4 with a detector C5 located opposite. The CT system C1 further includes a patient table on which patient C25 can be moved into the field of view during the examination along a system axis C9. The scanning itself can be done as a pure circular scan, without the patient being pushed forward, or during movement of the patient table as a spiral scan. The movement of the patient table C8 relative to the gantry is effected by a suitable motorization. During this movement, the x-ray sources C2 and C4 as well as the detectors C3 and C5 rotate around the patient, while acquiring projection data, which is then used for the reconstruction of sectional images. As alternative to a sequential scan, in which the patient is pushed step-by-step through the examination field between individual scans, there is also the possibility of the spiral scan, in which the patient is continuously moved along the system axis C9 during rotation and scanning of the x-ray tubes C2 and C4 and detectors C3 and C5.

The CT system C1 is controlled by a control and calculation unit C10. From the control and calculation unit C10, it is possible, via an interface 24, for acquisition control signals AS to be transferred in order to actuate the CT system in accordance with specific measurement protocols. The acquisition control signals AS may, for example, control the x-ray tubes as well as the gantry, for example the rotational speed and the patient table advance movement.

The measured projection data p, also called as raw data, is transferred via a raw data interface C23 to the control and calculation unit C10. The projection data p is then, if appropriate after a suitable pre-processing, further processed in a data processing unit C21, which can be a parallel processor suitable for performing multiple calculations simultaneously. The data processing unit C21 has access to first and second data storage units C22, C24, respectively. C22 is a permanent memory, such as a hard disc, whereas C24 is a working memory, as known in the art of computers. The calculation unit C10 may also have a reader of data carriers, for example a CD-ROM drive or USB-entry for reading USB-sticks. Thereby, computer program code Prg can be loaded onto the calculation unit C10, for example on an optical data carrier C26, such as a CD-ROM. Alternatively, such program code Prg can also be entered into the memory C22 of the calculation unit C10 via a network connection such as WiFi, which optionally may be connected to the internet.

The method of the invention may be contained in such program code Prg, and may cause the calculation unit C10, and in particular the data processing or image reconstruction component C21 together with the data storage units C22 and C24, to perform the method according to the invention on the projection data p. Any intermediate image datasets may be stored in the working memory 24, or alternatively in the first data storage unit C22. The final image dataset can also be saved in the second data storage unit and may further be viewed on the display C27.

The calculation unit C10 does not have to be located in the vicinity of the CT system C1 (as shown in FIG. 1). Instead, it can be accommodated in another room or even further away, wherein the transfer of the projection data can be carried out through a wire or by radio.

Alternatively, the calculation unit C10 may be entirely disconnected from the CT system, so that it does not provide control signals AS for the acquisition, but it may be implemented as any standalone computer.

Figure 2:
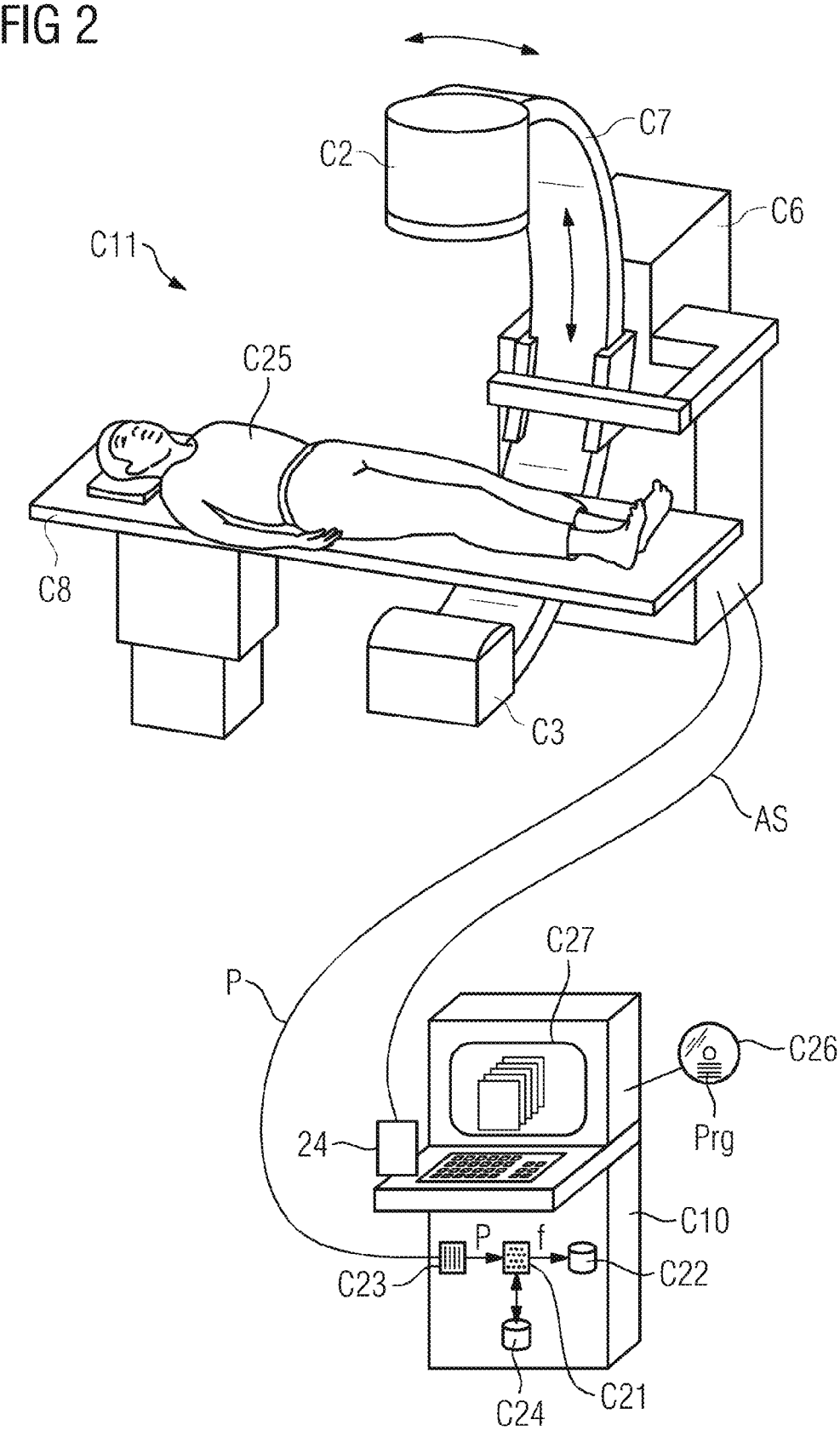
FIG. 2 shows a schematic representation of a second example embodiment of a computed tomography system having an image construction facility.

FIG. 2 shows a C-arm system C11, which can also be used to acquire projection data p to be reconstructed with a method according to the invention. In the C-arm system, in contrast to the CT system of FIG. 1, the housing C6 carries the C-arm C7. On the ends of the C-arm, opposing to each other, are mounted the x-ray tube C2 and the detector C4. For a scanning procedure, the C-arm C7 is likewise rotated around the patient, so that projection data p can be acquired from a plurality of projection angles. In this case, the projection data will be cone beam data, so that the reconstructed images will be 3D, rather than 2D, as is the case in the CT system of FIG. 1. The C-arm system C11 is provided with a control and calculation unit C10 of the type described in connection with FIG. 1.

Figure 3:
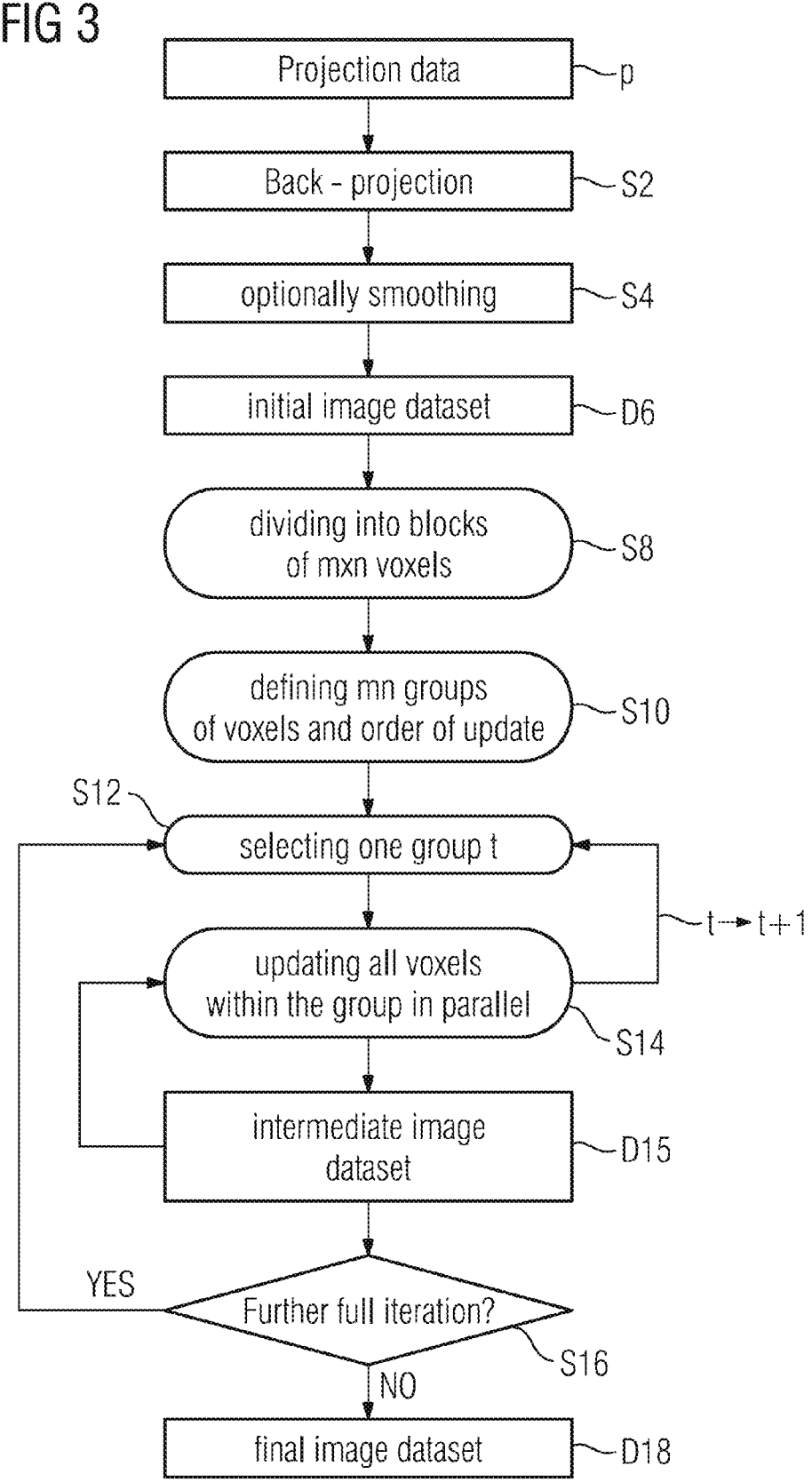
FIG. 3 shows a flow diagram of an embodiment of the inventive method.

FIG. 3 shows an example embodiment of the inventive method. The input data is projection data p, which may be acquired by one of the CT systems C1 or C11 shown in FIGS. 1 and 2. The projection data may be incomplete.

A simple back-projection step S2 is then carried out on the projection data p, and which may be for example filtered back-projection or any other standard back-projection method. The image thus obtained is optionally smoothed with a soft-focus effect is step S4, since such filtering may lead to a faster convergence of the iterative reconstruction method according to the invention.

Figures 4, 5:
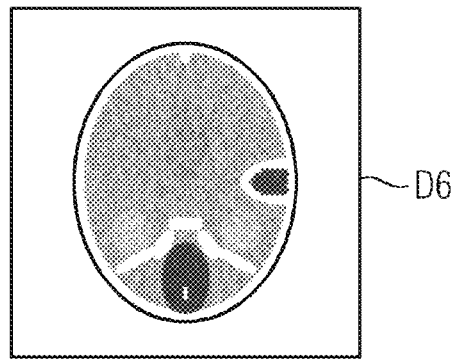
FIG. 4 shows an initial image reconstructed by filtered back-projection.
FIG. 5 shows a schematic representation of an initial image dataset according to an embodiment of the invention, divided into 3×3 blocks of voxels, each having m×m voxels, where m=4.

FIG. 4 shows an example of such a smoothed initial image dataset D6, namely a computer-simulated data of the FORBILD head phantom, which was created in fan-beam geometry using a curved detector array. This example projection dataset consisted of 1160 projections uniformly distributed over 360 degrees, with 340 rays per projection. The beam width was 0.075 cm at field-of-view center and the scan radius was 57 cm. Each measurement was simulated as an average over five line integrals that were calculated each using analytical expressions. The average was introduced to mitigate the effect of high-frequency errors in the reconstruction process. Noise was added to the data using a Poisson model assuming an emission of 100,000 photons per ray.

The image was discretized into a set of 350×350 square pixels, the width of which was 0.075 cm. The link between the image and the measurements was formulated using the distance-driven method, as described in B. De Man and S.

Basu, "Distance-driven projection and backprojection in three dimensions," Physics in Medicine and Biology 49, pp. 2463-2474, 2004.

Returning to FIG. 3, the initial image dataset is divided into blocks of m×n, or alternatively m×m voxels or, in this case, pixels, in step S8. This is illustrated in FIG. 5, where n=4, so that the schematic dataset having 12×12 pixels 4 is divided into nine groups 2 having 4×4 pixels each.

Further, the groups of voxels or subspaces are defined in step S10. Each group 2 is defined by selecting one element out of each block, using the same element position from one block to the next. For example, the shaded pixels 6 in FIG. 5 (having a pixel update in sub-iteration 7 and 25) define one subspace.

The voxel values are then updated group by group, following in at least one embodiment a pre-determined order. FIG. 5 demonstrates one possible order of updating, namely starting with the pixels in the left upper corner, then going to the right, down a row, to the left and so forth up to the voxels in the lower right corner (labeled 16). Voxels are then again updated in reverse order up to voxel 1=voxel 31. Thus, one full iteration in this schematic example of FIG. 5 corresponds to 31 sub-iterations.

Returning to FIG. 3, this step S12 is performed by selecting one group or subspace having the counter t out of the mn or m2 subspaces in step S12, and updating all voxels within this group in parallel, step S14. The counter t is then increased by 1, so that the next group of voxels is updated. In the example of FIG. 5, t would be increased from 1 up to 31. After each sub-iteration S14, the updated voxel values are written into an intermediate image dataset D15, which is then used as input for the next sub-iteration. After one full iteration has been done, depending for example on whether a certain threshold is reached in the difference between the calculated (forward-projected) projection dataset and the measured projection data, either a further full iteration is performed (step S16), or the last intermediate image dataset is made the final image dataset D18. This final image dataset may be displayed or otherwise outputted for the user.

Mathematically, step S14 of updating all voxel values within one group may be described as follows:

Let x be the vector of unknown image coefficients, e.g. the unknown 2D or 3D image datset, let g be the vector grouping the CT measurements, e.g. the projection data, which may be a sinugram, fan-beam or cone-beam dataset, and let A be the matrix that links x to the CT measurements, e.g. the "projector" or forward projection matrix which simulates the geometry of the data acquisition process, as defined by a basis function or by an interpolation model such as the Joseph's method described in P. M. Joseph, "An Improved Algorithm for Reprojecting Rays Through Pixel Images," IEEE Transactions on Medical Imaging 1, pp. 192-196, November 1982 (the entire contents of which are hereby incorporated herein by reference), or the distance driven method. In at least one embodiment of the invention, the desired image can be defined as $$x^* = \arg\min\{\Phi(x,g) = \Phi_1(x,g) + \beta\Phi_2(x)\}$$

The first term, $\Phi_1(x,g)$ includes the measurement statistics and the geometry of the data acquisition process. In one embodiment of the inventive method, one uses $$\Phi_1(x,g) = \|W(Ax-g)\|^2$$

which corresponds to a weighted least-square model. W is a statistical matrix which includes information e.g. about the data redundancy, the data statistics and might include a bowtie filter. Preferably, A is the projection operator, which maps the projection geometry of the CT-system, and x is the image dataset (initial, intermediate or final).

The second term, $\Phi_2(x)$, may be a non-linear regularization term that mitigates noise and artifacts. Parameter β>0 controls the strength of $\Phi_2(x)$. β is the weighting factor of the weighted sum, and may be between 0 and 10, it may also be 1. In at least one embodiment of the inventive method, expressions of $\Phi_2(x)$ are used which allow $\Phi(x)$ to be convex and only link the voxels to their immediate neighbors.

In at least one example, the expression for the regularization term may be $$\Phi_2(x) = \sum_j \frac{1}{2} \sum_i \omega_{ij} \psi(x_i - x_j)$$

where $\omega_{ij}$ is a positive geometry-based scalar. One may set $\omega_{ij}=1$ for pixels which are neighbors horizontally and vertically, $\omega_{ij}=1/\sqrt{2}$ for diagonally neighboring pixels and $\omega_{ij}=0$ otherwise. The Fair potential function can be used to define $\psi(t)$, i.e.

$$\psi(t) = \delta^2 \cdot \left[\left|\frac{t}{\delta}\right| - \log\left(1 + \left|\frac{t}{\delta}\right|\right)\right]$$

FISTA is a fast converging algorithm. This method generates the following sequence of iterates:

$$x^k = \arg\min\left\{\frac{L}{2}\left\|x - \left(\tilde{x}^k - \frac{1}{L}\nabla\Phi_1(\tilde{x}^k, g)\right)\right\|^2 + \beta\Phi_2(x)\right\}$$

$$\tilde{x}^{k+1} = x^k + \left(\frac{t_k - 1}{t_{k+1}}\right)(x^k - x^{k-1}), \text{ and}$$

$$t_{k+1} = \frac{1 + \sqrt{1 + 4t_k^2}}{2}$$

where L is a Lipschitz constant for $\Phi_1$. The sequence can be initiated using $t_1=1$ and $\tilde{x}^1=x^0$ In at least one embodiment, for each sub-iteration, parameter L can be shown to be equal to $2\sigma_{max}$, where $\sigma_{max}$ is the maximum singular value of the sub-projection matrix; $\sigma_{max}$, and thereby L, was estimated using the Power method, see for example G. H. Golub and C. F. van Loan, "Matrix computations," John Hopkins University Press, 1996, the entire contents of which are hereby incorporated herein by reference.

Figure 6:
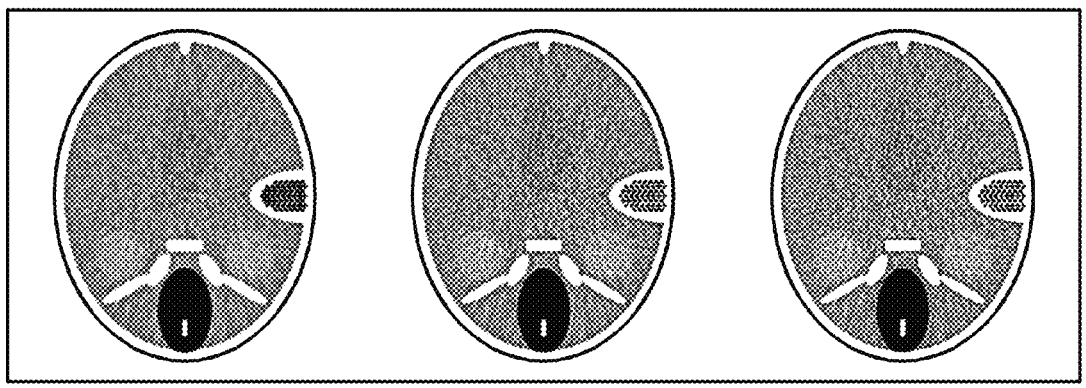
FIG. 6 shows images reconstructed using an embodiment of the inventive method using one full iteration. The images form top to bottom correspond to m=2, 3, 4. Gray scale: [−50, 155] HU.
Figure 7:
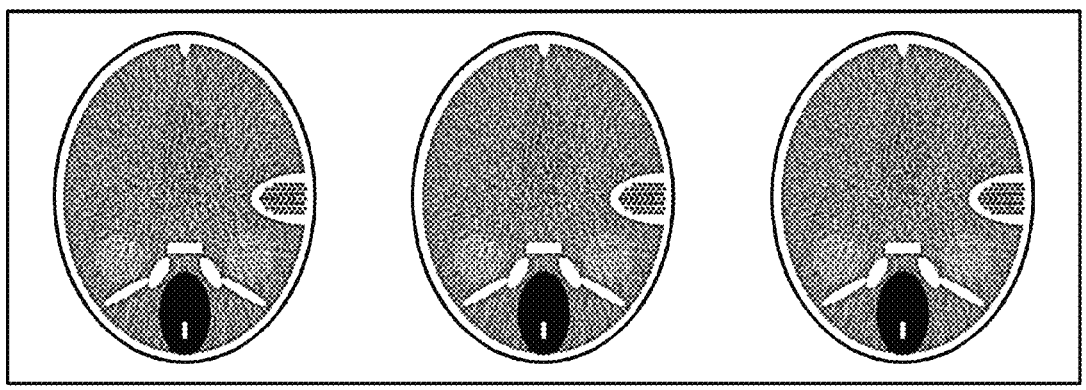
FIG. 7 shows images reconstructed according to an embodiment of the inventive method using two full iterations. The images from top to bottom correspond to m=2, 3, 4. Gray scale: [−50, 155] HU.

In the example the results of which are shown in FIGS. 6 and 7, δ=0.004 and β=5.0 was selected, which allow reasonable regularization, but these are not task-based optimized values.

Figure 8:
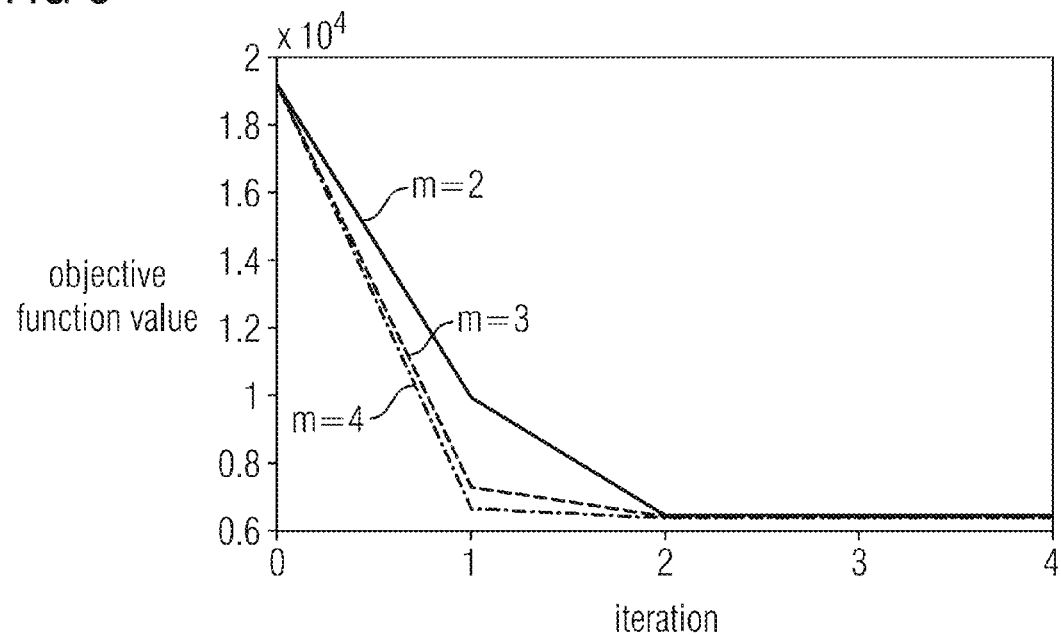
FIG. 8 shows a plot of objective function value versus the number of full iterations for m=2, 3, 4.
Figure 9:
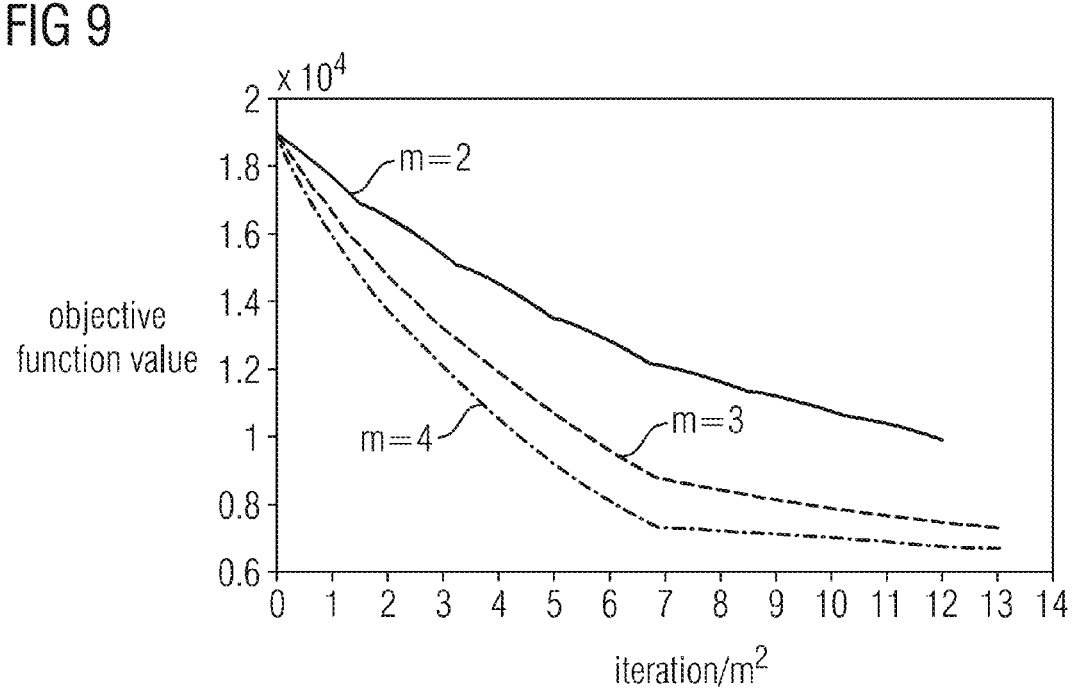
FIG. 9 shows a plot of objective function value as a function of the number of sub-iterations over m2 within the first full iteration for m=2, 3, 4.

FIGS. 6 and 7 show reconstructed images after one and two full iterations. The decrease of the objective function for the first four full iterations is shown in FIG. 8, whereas FIG. 9 shows reduction in the objective function within the first full iteration, i.e., from one sub-iteration to the next. These reductions correspond to stopping the sub-iterations when the difference in the objective function becomes smaller than $10^{-5}$, with the embedded Newton-Raphson method being stopped when the objective function changes by less than $10^{-6}$.

TABLE 1

Normalized relative time measurements for the first 8 sub-iterations for the block sizes m = 2; 3; 4, and also for one full iteration.

|  | m = 2 | m = 3 | m = 4 |
|---|---|---|---|
| 8 first sub-iteration | 1.00 | 0.25 | 0.13 |
| first full iteration | 1.00 | 0.46 | 1.97 |
| (number of sub-iterations) | (49) | (119) | (208) |

Table 1 shows some initial computation effort measurements for a non-optimized implementation of the algorithm on a Laptop equipped with an Intel® i5 CPU Core™ and a 64-bit operating system.

Each of these measurement was first averaged over 10 independent runs and then normalized with the time measurement for m=2. In this particular embodiment, one observes that sub-iterations for the block size m=4 in average are much faster compared to sub-iterations for m=3 and m=2, respectively. This observation is due to the size of the sub-iteration projection matrix that is $1/m^2$ smaller than a full projection matrix which is applied to a whole image. Consequently, the bigger the block size m the less calculations needs to be done within one sub-iteration.

Second, it was observed that a block size of m=3 gives a very good time measurement over all sub-spaces (1 full iteration). Since in this embodiment the "back-and-forth" approach was used, there are altogether 7 sub-spaces for m=2, 17 sub-spaces for m=3 and 31 sub-spaces for m=4. Therefore, the relative time measurement results for a full iteration appear to represent a tradeoff between the number of sub-iteration steps, the number of necessary calculations defined by the size of the sub-iteration projection matrix and between the number of sub-spaces. However, these results may vary for other embodiments of the invention.

The initial results convey a fast convergence rate. After 3 iterations, changes in the reconstructed image were tiny ($10^{-2}$ HU) indicating convergence. Some differences were observed in the way the objective function decreases and the subjective image impression depending on m, the size of the block defining the voxel groups. The computational effort appeared to be also dependent on m.

At least one embodiment of the present inventive method combines the strengths of FISTA and block-based iterative descent methods to achieve a fast iterative CT reconstruction with convenient parallelization capability. The method and algorithm can be applied to any convex problem of the form $x^* = \arg\min \{\Phi(x, g) = \Phi_1(x, g) + \beta\Phi_2(x)\}$.

Thus, it could be shown that the method according to the invention converges, and that each subspace update is obtained with a converging rate that is quadratic. The experimental results have further shown that the first loop, which jumps from one subspace to the next, is converging very fast, due to the decoupling between the subspaces.

The example embodiments described hereto for relate to the medical application of the invention. The embodiments of the invention can, however, be used outside the medical sector, for example in the examination of baggage, or the investigation of material.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

The invention has been described hereto for on the basis of example embodiments. It is understood that many changes and modifications are possible, without departing from the framework of the invention.

REFERENCE NUMBERS

C1 Computed tomography system
C2, C4 X-ray sources
C3, C5 X-ray detectors
C5 Gantry
C6 Gantry housing
C7 C-arm
C8 Patient table
C9 System axis
C10 Control and calculation unit
C11 C-arm computed tomography system
C21 Data processing unit
C22 Hard disc
C23 Raw data interface
C24 Working memory
C26 Optical data carrier
C27 Display
24 Interface
AS Control signals
p raw projection data
f Final image data set
Prg Program code
S2, S6, S10,
S12, S14, S16 Method steps
D6 Initial image dataset
D15 Intermediate image dataset
D18 Final image dataset
2 Block
4 Voxel
6 Voxels belonging to one group

What is claimed is:

1. A method for reconstructing an image dataset of an object from projection data, the projection data being acquired from the object via an x-ray computed tomography system, the method comprising:
reconstructing an initial image dataset from the projection data via a back-projection method;
dividing the initial image dataset into blocks of voxels, each of the blocks having at least approximately the same size;
defining groups of voxels within the image dataset, each of the groups being defined by selecting one voxel from each of the blocks, each voxel within one of the groups having a same position relative to other voxels within the corresponding block, wherein the voxels within one of the groups define a subspace;
updating values of the voxels for all voxels within the one of the groups by minimizing a function including a weighted sum of a first term representing at least a geometry of a data acquisition process and a second term, to thereby generate an intermediate image dataset, the first term of the weighted sum including information on data statistics, data redundancy and hardware fillers inserted in front of an x-ray source of the x-ray computed tomography system; and
repeating the updating of the voxel values for all voxels within the one of the groups, using the intermediate image dataset as input, until all groups of voxels have been updated at least once, whereby a final image dataset is obtained.

2. The method of claim 1, wherein the updating of the voxel values for all voxels within the one of the groups is carried out by updating all voxels in parallel.

3. The method of claim 1, wherein the blocks of voxels are contiguous.

4. The method of claim 1, wherein the blocks of voxels are not contiguous.

5. The method of claim 1, wherein the updating is performed by exactly solving an optimization problem corresponding to minimizing the function.

6. The method of claim 1, wherein the updating of the voxel values for all voxels within the one of the groups is done while keeping all other voxel values constant.

7. The method of claim 1, wherein one full iteration is performed by repeating the updating of the voxel values for all voxels within the one of the groups until all groups of voxels have been updated once or twice in an order.

8. The method of claim 7, wherein one or several full iterations are performed.

9. The method of claim 8, wherein the updating of the voxel values for all voxels within the one of the groups includes minimizing the function until a threshold is reached.

10. The method of claim 9, wherein the threshold is either a constant or a variable varying from one full iteration to a subsequent full iteration.

11. The method of claim 1, wherein the updating of the voxel values for all voxels within the one of the groups includes minimizing the function until a threshold is reached.

12. The method of claim 11, wherein the threshold is one of a constant or a variable varying from one full iteration to a subsequent full iteration.

13. The method of claim 1, wherein the updating of the voxel values for all voxels within the one of the groups is done using a Fast Iterative Shrinkage-Thresholding Algorithm (FISTA).

14. The method of claim 1, wherein the first term is a least squares expression representing the geometry of the data acquisition process.

15. The method of claim 1, wherein the first term is minimized using an iterative method, wherein in each iteration, the image dataset is forward projected to obtain a calculated projection dataset, a difference between the calculated projection dataset and the projection data is determined, the difference is backward projected, and the backward projection is weighted and subtracted from or added to the image dataset.

16. The method of claim 1, wherein the first term is minimized by using a Landweber algorithm.

17. The method of claim 1, wherein the second term is a non-linear, regularization term.

18. The method of claim 1, wherein the second term of the weighted sum relates each voxel to corresponding neighboring voxels.

19. The method of claim 1, wherein the second term is minimized using a Newton-Raphson algorithm.

20. The method of claim 1, wherein the groups of voxels are updated in an order.

21. The method of claim 20, wherein the groups of voxels are updated within one full iteration by updating first ones of the voxels in a first corner of each block followed by updating adjoining voxels towards second ones of the voxels in a corner opposite the first corner, followed by reverse updating the first ones of the voxels in the first corner of each block, whereby all voxels are updated twice, except the second ones of the voxels in the opposite corner.

22. The method of claim 1, wherein the first image dataset is subjected to a smoothing filtering processing prior to being divided into blocks.

23. A device configured to reconstruct an image dataset of an object from projection data, carrying out the method claimed in claim 1, the device comprising:
 a first memory configured to store the projection data and the final image dataset;
 a second memory configured to store the intermediate image datasets;
 a processor configured to reconstruct the first image dataset, define groups of voxels within the first image dataset and update the voxel values for all voxels; and
 an image dataset interface configured to output the final image dataset.

24. A computed tomography system, comprising:
 a projection data acquisition unit, including an x-ray source and a detector, configured to acquire projection data of an object; and
 the device of claim 23.

25. A non-transitory computer-readable medium comprising computer-readable instructions, which when executed by a processor, causes the processor to perform the method of claim 1.

* * * * *